(12) United States Patent
Sato et al.

(10) Patent No.: US 6,581,370 B2
(45) Date of Patent: Jun. 24, 2003

(54) FAILURE DETERMINATION DEVICE FOR HUMIDITY SENSOR AND CONTROL SYSTEM FOR EXHAUST PASSAGE CHANGEOVER VALVE

(75) Inventors: Masahiro Sato, Saitama-ken (JP); Yoshihisa Iwaki, Saitama-ken (JP); Masaki Ueno, Saitama-ken (JP); Shusuke Akazaki, Saitama-ken (JP); Takashi Haga, Saitama-ken (JP); Tadashi Sato, Saitama-ken (JP); Yasuyuki Miyahara, Saitama-ken (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/985,764

(22) Filed: Nov. 6, 2001

(65) Prior Publication Data

US 2002/0053199 A1 May 9, 2002

(30) Foreign Application Priority Data

Nov. 6, 2000 (JP) .......................................... 2000-338376
Nov. 6, 2000 (JP) .......................................... 2000-338377

(51) Int. Cl.$^7$ ................................................ F01N 3/00
(52) U.S. Cl. ............................ 60/277; 60/278; 60/287; 60/291; 60/297; 123/688; 73/118.1
(58) Field of Search .......................... 60/277, 276, 287, 60/288, 289, 278, 297, 299, 291; 123/479, 688; 73/118.1

(56) References Cited

U.S. PATENT DOCUMENTS

| 4,993,386 A | * | 2/1991 | Ozasa et al. ................. 123/417 |
| 5,735,245 A | * | 4/1998 | Kubesh et al. .............. 123/417 |
| 6,357,227 B1 | * | 3/2002 | Neufert ........................ 60/309 |

FOREIGN PATENT DOCUMENTS

| JP | 356006041 A | * | 1/1981 | .................. 123/703 |
| JP | 05-256124 | * | 10/1993 | ................... 60/287 |

* cited by examiner

Primary Examiner—Thomas Denion
Assistant Examiner—Binh Tran
(74) Attorney, Agent, or Firm—Arent Fox Kintner Plotkin & Kahn, PLLC

(57) ABSTRACT

A failure determination device that detects the humidity of exhaust gases from an internal combustion engine and a control system for an exhaust passage changeover valve, which can switch the changeover valve with appropriate timing, thereby enabling sufficient purification of exhaust gases. An operating condition of the engine is detected. Based on the detected operating condition of the engine, it is determined whether the engine is in an operating condition in which failure determination of the humidity sensor can be executed. It is determined whether the humidity sensor has failed, based on a result of detection by the humidity sensor, when it has been judged that the failure determination of the humidity sensor can be executed.

15 Claims, 13 Drawing Sheets

FAILURE DETERMINATION DEVICE FOR HUMIDITY SENSOR AND CONTROL SYSTEM FOR EXHAUST PASSAGE CHANGEOVER VALVE

BACKGROUND OF THE INVENTION

1. Field of the Invention

This invention relates to a failure determination device for a humidity sensor that detects humidity of exhaust gases from an internal combustion engine and a control system for controlling an exhaust passage changeover valve capable of switching an exhaust passage for exhaust gases from the engine between a main exhaust passage and a bypass exhaust passage having an adsorber capable of adsorbing hydrocarbons and water contained in the exhaust gases.

2. Description of the Prior Art

Generally, in the exhaust system of a gasoline engine or the like, a three-way catalyst is arranged in an intermediate portion of the exhaust pipe in order to purify harmful substances (hydrocarbons, carbon monoxide and nitrogen compounds) in exhaust gases. However, immediately after the engine is started in a cold condition (e.g. before approximately 30 to 40 seconds have passed after the cold start of the engine), for instance, the three-way catalyst remains inactive, and the harmful substances cannot be purified sufficiently, so that particularly hydrocarbons are emitted from the engine as unburned combustible components. Therefore, in order to prevent emission of such hydrocarbons into the air, there has been proposed an engine which has, in addition to the three-way catalyst, an adsorber arranged in the exhaust pipe, for adsorbing hydrocarbons. Such an adsorber is arranged in a bypass exhaust passage which is branched from an intermediate portion of a main exhaust passage of the exhaust pipe having the three-way catalyst arranged therein. A changeover valve arranged in a bifurcating portion of the exhaust pipe switches the exhaust passage for exhaust gases between the main exhaust passage and the bypass exhaust passage. Thus, exhaust gases emitted immediately after the cold start of the engine are purified by the adsorber adsorbing hydrocarbons, and then discharged into the air.

The above-mentioned adsorber carries a zeolite on its surface. When exhaust gases are passing through the bypass passage, the molecules of hydrocarbons enter small holes of the zeolite whereby the hydrocarbons are adsorbed by the adsorber. The adsorber of this kind desorbs hydrocarbons once adsorbed thereby when it is heated to a temperature equal to or higher than a predetermined temperature (e.g. 100 to 250° C.). The desorbed hydrocarbons are recirculated to the engine e.g. via the EGR. As described above, the adsorber repeatedly carries out adsorption and desorption of hydrocarbons. However, the amount of undesorbed hydrocarbons permanently remaining in the adsorber may progressively increase or the small holes of the adsorber may be destroyed by a long-term use thereof. This results in the degradation of the adsorber, that is, a lowered adsorbing capacity of the adsorber for adsorbing hydrocarbons. If the engine is repeatedly started in such a state, an increasing amount of unadsorbed hydrocarbons is emitted into the air. Therefore, to carry out engine control for desorbing hydrocarbons (e.g. by elevating the temperature of the adsorber) to cope with the degraded state of the adsorber, or to notify the driver of the degradation of the adsorber, the present assignee has already proposed a degradation-detecting device for detecting degradation of a hydrocarbon adsorber by Japanese Patent Application No. 2000-66443.

In this degradation-detecting device, a humidity sensor is arranged at a location downstream of an adsorber in a bypass exhaust passage such that the humidity of exhaust gases having passed through the adsorber is detected by the humidity sensor, and degradation of the adsorber is detected based on the result of the detection. This degradation-detecting device utilizes proportionality between the adsorber's capabilities of adsorbing hydrocarbons and of adsorbing water. By detecting the humidity of exhaust gases having passed through the adsorber by using the humidity sensor, it becomes possible to detect lowered adsorbing capability of the adsorber for adsorbing hydrocarbons and water, that is, degradation of the adsorber.

Although the above degradation-detecting device can properly detect the degradation, once the humidity sensor of the degradation-detecting device has failed, the proper detection of the degradation cannot be performed, making it impossible to suitably carry out engine control or notify the driver of the degradation of the adsorber. Therefore, the conventional degradation-detecting device has room for improvement in this respect.

A control system of the above-mentioned kind has been proposed e.g. by Japanese Laid-Open Patent Publication (Kokai) No. 11-2115. The proposed control system includes a temperature sensor disposed in the exhaust pipe at a location between the three-way catalyst and the changeover valve, for detecting an exhaust temperature on a downstream side of the three-way catalyst, and based on the result of detection by the temperature sensor, controls the changeover valve in the following member: An exhaust temperature detected by the temperature sensor, and a predetermined temperature (e.g. 300° C.) defined in advance are compared with each other. When the exhaust temperature is lower than the predetermined temperature, it is determined that the three-way catalyst remains inactive, and the main exhaust passage is closed and at the same time the bypass exhaust passage is opened by the changeover valve. Thus, the exhaust gases are guided into the bypass exhaust passage, for causing hydrocarbons in the exhaust gases to be adsorbed by the adsorber, whereby the exhaust gases are purified. On the other hand, when the exhaust temperature is higher than the predetermined temperature, it is determined that the three-way catalyst has been activated, and the bypass exhaust passage is closed and at the same time the main exhaust passage is opened by the changeover valve, whereby the exhaust gases purified by the three-way catalyst are emitted without farther processing. It should be noted that the above adsorber adsorbs hydrocarbons when it is in a low temperature condition (e.g. lower than 100° C.) while desorbing the hydrocarbons once adsorbed thereby at temperatures equal to or higher than a predetermined temperature (e.g. 100 to 250° C.). The desorbed hydrocarbons are recirculated to the engine e.g. via an EGR pipe.

As described hereinabove, in the control system for the changeover valve, the exhaust temperature on the downstream side of the three-way catalyst is detected by the temperature sensor, and the condition of the three-way catalyst is estimated based on the result of the detection so as to control the changeover valve. In the above control system, however, the changeover valve is controlled irrespective of the actual state of adsorption of hydrocarbons by the adsorber. Moreover, generally, a temperature detected by the temperature sensor is slow in change, has low responsiveness, and is liable to be adversely affected by parameters including an outside air temperature, and the like. Therefore, in the above control system, it is sometimes impossible to control the changeover valve with appropriate timing, which causes insufficient purification of exhaust gases.

SUMMARY OF THE INVENTION

It is a first object of the invention to provide a failure determination device which is simple in construction and capable of properly determining failure of a humidity sensor that detects the humidity of exhaust gases from an internal combustion engine.

It is a second object of the invention to provide a control system for an exhaust passage changeover valve, which is capable of switching the changeover valve with appropriate timing, thereby making it possible to sufficiently purify exhaust gases.

To attain the first object, according to a first aspect of the invention, there is provided a failure determination device for a humidity sensor that detects humidity of exhaust gases from an internal combustion engine.

The failure determination device according to the first aspect of the invention is characterized by comprising:

operating condition-detecting means for detecting an operating condition of the engine;

failure determination execution-judging means for judging whether or not the engine is in an operating condition in which failure determination of the humidity sensor can be executed, based on a result of detection by the operating condition-detecting means; and humidity sensor failure-determining means for determining whether or not the humidity sensor has failed, based on a result of detection by the humidity sensor, when the failure determination execution-judging means judged that the failure determination of the humidity sensor can be executed.

According to this failure determination device, when the failure determination execution-judging means judged that the engine is in an operating condition in which failure determination of the humidity sensor can be executed, depending on the operating condition of the engine, the humidity sensor failure-determining means determines whether or not the humidity sensor has failed, based on the result of detection by the humidity sensor. Depending on the operating condition of the engine, if a value of humidity detected by the humidity sensor is not within a predetermined range in spite of the engine being in a predetermined operating condition wherein the detected value should be within the predetermined range, it is possible to determine that the humidity sensor has failed. This makes it possible to properly determine failure of the humidity sensor with appropriate timing. Further, the determination of failure of the humidity sensor is carried out by using a humidity value detected by the humidity sensor, and hence it is possible to implement a failure determination device for determining a failure of the humidity sensor by relatively simple construction without any need for a special device.

Preferably, an exhaust passage for the exhaust gases is configured such that the exhaust passage can be switched between a main exhaust passage and a bypass exhaust passage having an adsorber arranged in an intermediate portion thereof, the adsorber being capable of adsorbing hydrocarbons and water in the exhaust gases, the humidity sensor being arranged at a location downstream of the adsorber in the bypass exhaust passage, and the failure determination execution-judging means judges that the failure determination of the humidity sensor can be executed when the exhaust passage has been switched to the bypass exhaust passage, and at the same time the adsorber is adsorbing hydrocarbons in the exhaust gases guided into the bypass exhaust passage.

According to this preferred embodiment, the humidity sensor is arranged at a location downstream of the adsorber in the bypass exhaust passage, and hence it is possible to detect the humidity of exhaust gases having passed through the adsorber which is performing adsorbing operation, more specifically, the humidity of exhaust gases (post-adsorption exhaust gases) whose hydrocarbons and water have been adsorbed by the adsorber. Thus, when the exhaust gases are guided into the bypass exhaust passage and at the same time the adsorber is adsorbing hydrocarbons in the exhaust gases, the failure determination execution-judging means judges that failure determination of the humidity sensor can be executed. Since the adsorber's adsorbing capabilities of adsorbing hydrocarbons and of water are proportional to each other, the humidity of the post-adsorption exhaust gases has close correlation with an actual state of adsorption of hydrocarbons by the adsorber. Therefore, so long as the adsorber is adsorbing hydrocarbons, a value of the humidity detected by the humidity sensor should be within the predetermined range e.g. when the adsorption of hydrocarbons is nearing completion. This enables the failure of the humidity sensor to be determined based on a value of the humidity detected by the humidity sensor. As described hereinabove, when the adsorber is adsorbing hydrocarbons, it is determined that the engine is an operating condition suitable for carrying out failure determination of the humidity sensor, whereby failure of the humidity sensor can be determined properly.

More preferably, the hydrocarbons are desorbed from the adsorber by switching the exhaust passage to the main exhaust passage, and the failure determination device further comprises desorption state-detecting means for detecting a state of desorption of the hydrocarbons from the adsorber, the failure determination execution-judging means judging whether or not the failure determination of the humidity sensor can be executed, based on the state of the desorption of the hydrocarbons from the adsorber at a time of termination of a preceding operation of the engine, detected by the desorption state-detecting means.

According to this preferred embodiment, it is judged whether or not failure determination of the humidity sensor can be executed, based on a state of desorption of the hydrocarbons from the adsorber, which is detected by the desorption state-detecting means at a time of termination of a preceding of operation of the engine. Therefore, appropriate failure determination can be executed by taking into account the state of desorption of hydrocarbons from the adsorber, which affects a value of humidity detected by the humidity sensor. More specifically, for instance, if desorption of hydrocarbons had not been completed during the immediately preceding operation of the engine, manners of changes in values detected by the humidity sensor become different so as to advance or retard timing of proper execution of the failure determination from a predetermined one. In such a case, according to this preferred embodiment, the failure determination is not executed, but only when desorption of hydrocarbons had been completed during the immediately preceding operation of the engine, the failure determination is caused out, whereby it is possible to prevent erroneous failure determination of the humidity sensor.

More preferably, the failure determination execution-judging means further includes timer means for measuring a time period after a start of the engine, and determines whether or not failure determination of the humidity sensor can be executed further based on the time period measured by the timer means.

Further preferably, the failure determination execution-judging means further includes fuel injection time-integrating means for calculating a cumulative value of fuel injection time periods after a start of the engine, and determines whether or not failure determination of the humidity sensor can be executed further based on the cumulative value calculated by the fuel injection time-integrating means.

Preferably, the humidity sensor failure-determining means determines that the humidity sensor has failed when the value of humidity detected by the humidity sensor is lower than a predetermined value.

To attain the second object, according to a second aspect of the invention, there is provided a control system for controlling an exhaust passage changeover valve of an internal combustion engine, the changeover valve switching an exhaust passage having a catalytic device arranged therein for purifying exhaust gases from the engine between a main exhaust passage and a bypass exhaust passage bypassing the main exhaust passage and having an adsorber arranged therein which is capable of adsorbing hydrocarbons and water in the exhaust gases.

The control system according to the second aspect of the invention is characterized by comprising:

a humidity sensor arranged at a location downstream of the adsorber in the bypass exhaust passage, for detecting humidity of the exhaust gases guided into the bypass exhaust passage; and changeover valve drive means for driving the changeover valve based on a result of detection by the humidity sensor.

According to this control system, the humidity sensor is arranged at a location downstream of the adsorber in the bypass exhaust passage, and hence it is possible to detect the humidity of exhaust gases having passed through the adsorber which is performing adsorbing operation, more specifically, the humidity of exhaust gases (post-adsorption exhaust gases) whose hydrocarbons and water have been adsorbed by the adsorber. Depending on the result of detection by the humidity sensor, the changeover valve is driven so as to switch the exhaust passage between the main exhaust passage and the bypass exhaust passage. Since the adsorber's capabilities of adsorbing hydrocarbons and of water are proportional to each other, the humidity of the post-adsorption exhaust gases has close correlation with an actual state of adsorption of hydrocarbons by the adsorber. Therefore, by detecting the humidity of the post-adsorption exhaust gases, it is possible to properly estimate whether or not the adsorption of hydrocarbons by the adsorber has been actually completed i.e. carried out to the limit of its capacity, and by controlling the switching operation of the changeover valve depending on the estimation, it is possible to switch the exhaust passage with appropriate timing, whereby the exhaust gases can be sufficiently purified.

Preferably, the control system further comprises delayed response compensation means for compensating for a delayed response of the humidity sensor.

According to this preferred embodiment, the delayed response of the humidity sensor is compensated for by the delayed response compensation means, whereby even if a humidity sensor actually used has low responsiveness, it is possible to control the switching operation of the changeover valve with more appropriate timing by compensating for the delayed response of such a humidity sensor.

Preferably, the humidity sensor includes a sensor element for being exposed to the exhaust gases for detecting humidity thereof, and the control system further comprises a heater for heating the sensor element, operating condition-detecting means for detecting an operating condition of the engine, and heater control means for controlling an operation of the heater depending on the operating condition detected by the operating condition-detecting means.

According to this preferred embodiment, the heater control means drives the heater depending on the operating condition of the engine, and the heater heats the sensor element of the humidity sensor, whereby the condition of the sensor element can be made suitable for detecting the humidity of the exhaust gases. For instance, there is a fear that condensation forms on the sensor element and coke or soot is deposited on the same to hinder proper detection of the humidity of the sensor element. Therefore, when the engine is in a condition in which the condensation and deposition are liable to occur, by heating the sensor element, the above inconveniences can be avoided, which enables the sensor to properly detect the humidity.

Preferably, the control system further comprises upstream-side humidity-estimating means for estimating humidity at a location upstream of the adsorber, based on a value of the humidity detected by the humidity sensor.

More preferably, the changeover valve drive means drives the changeover valve based on a difference between the value of the humidity detected by the humidity sensor and a value of the humidity estimated by the upstream-side humidity-estimating means.

Further preferably, the changeover valve drive means drives the changeover valve further based on a cumulative value of the difference between the value of the humidity detected by the humidity sensor and the value of the humidity estimated by the upstream-side humidity-estimating means.

Preferably, the control system further comprises an upstream-side humidity sensor for detecting humidity at a location upstream of the adsorber.

More preferably, the changeover valve drive means drives the changeover valve based on a difference between a value of the humidity detected by the humidity sensor and a value of the humidity detected by the upstream-side humidity sensor.

Further preferably, the changeover valve drive means drives the changeover valve further based on a cumulative value of the difference between the value of the humidity detected by the humidity sensor and the value of the humidity detected by the upstream-side humidity sensor.

The above and other objects, features, and advantages of the invention will become more apparent from the following detailed description taken in conjunction with the accompanying drawings.

BRIEF DESCRIPTION OF THE DRAWINGS

FIGS. 6A to 6C are diagrams showing schematic representations of changes in humidity as time elapses, which are useful in explaining the delayed response compensation process, in which:

FIG. 6A is a diagram showing an example of changes in (true value) of actual humidity on an upstream side of an HC adsorber;

FIG. 6B is a diagram showing an example of changes in humidity value detected by the humidity sensor on the upstream side of the HC adsorber; and FIG. 6C is a diagram showing an example of changes in corrected or compensated value of the detected humidity value;

FIGS. 11A to 11C are timing charts showing examples of changes in various data, from the time of the start of the engine, in which:

FIG. 11A is a diagram showing an example of changes in cumulative value of fuel injection time periods;

FIG. 11B is a diagram showing an example of changes in humidity on a downstream-side of the HC adsorber; and FIG. 11C is a diagram showing an example of changes in temperature of a sensor element;

DETAILED DESCRIPTION OF PREFERRED EMBODIMENTS

Figure 1:
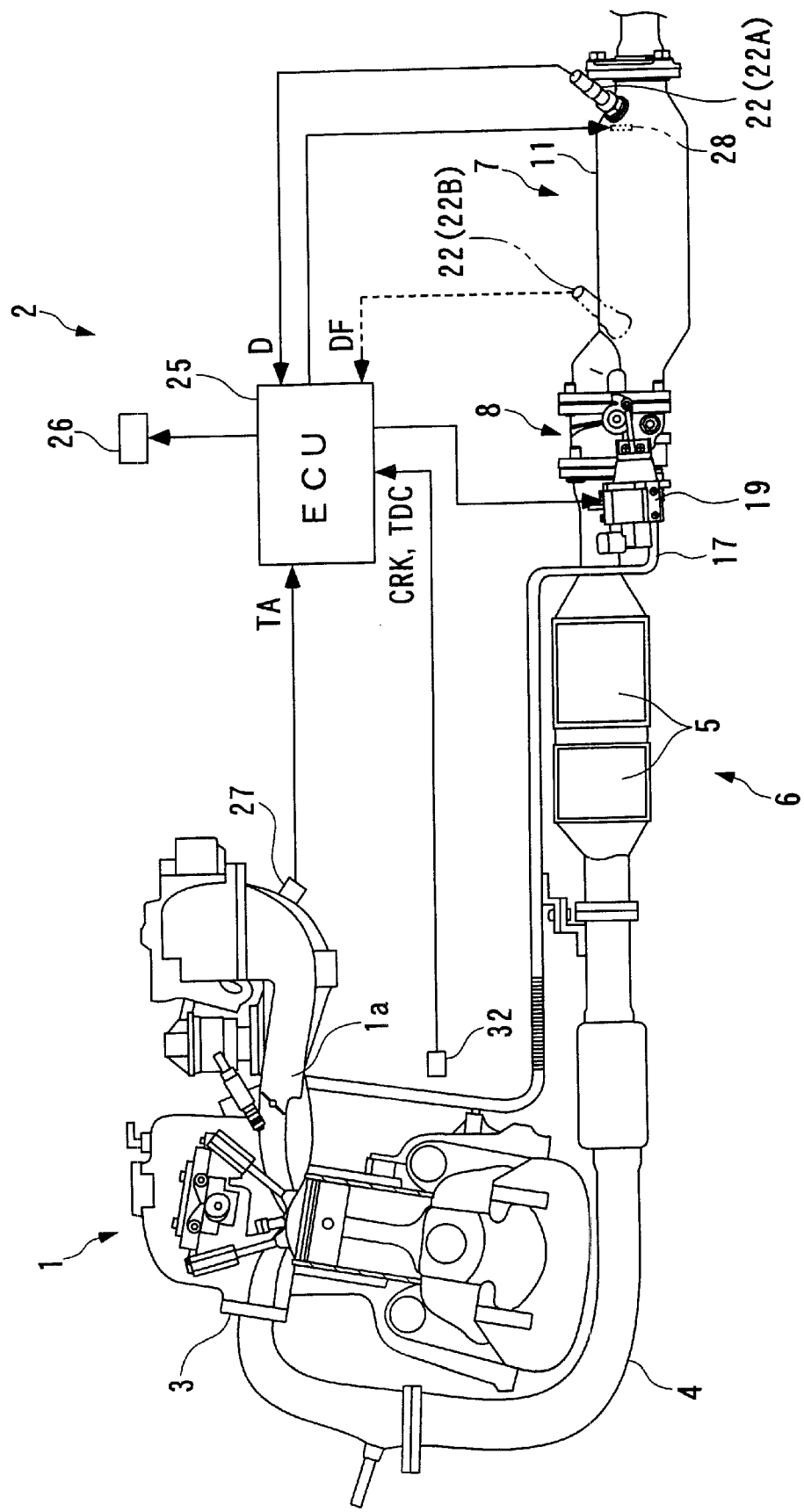
FIG. 1 is a block diagram schematically showing the arrangement of an internal combustion engine incorporating a failure determination device for determining failure of a humidity sensor and a control system for controlling an exhaust passage changeover valve, according to an embodiment of the invention.

The invention will now be described in detail with reference to the drawings showing preferred embodiments thereof. Referring first to FIG. 1, there is schematically shown the arrangement of an internal combustion engine to which are applied a failure determination device for determining failure of a humidity sensor, and a control system for controlling an exhaust passage changeover valve, according to an embodiment of the present invention. As shown in the figure, an exhaust system 2 of the internal combustion engine 1 (hereinafter simply referred to as "the engine 1") is configured such that exhaust gases from the engine 1 are discharged after being purified, and at the same time part of the exhaust gases (EGR) can be recirculated back to the engine 1. The exhaust system 2 has an exhaust pipe 4 connected to the engine 1 via an exhaust manifold 3.

A catalytic device 6 having two three-way catalysts 5, 5 and a hydrocarbon adsorption device 7 for adsorbing hydrocarbons are arranged in an intermediate portion of the exhaust pipe 4, as exhaust gas purification catalysts for purifying exhaust gases. The two three-way catalysts 5, 5 which are arranged in the catalytic device 6 along the exhaust pipe 4 in a manner adjacent to each other are activated by being heated to a temperature equal to or higher than a predetermined temperature (e.g. 300° C.), thereby purifying harmful substances (hydrocarbons, carbon monoxide and nitrogen compounds) in exhaust gases passing through the catalytic device 6 by oxidation-reduction catalytic actions thereof.

Figure 2:
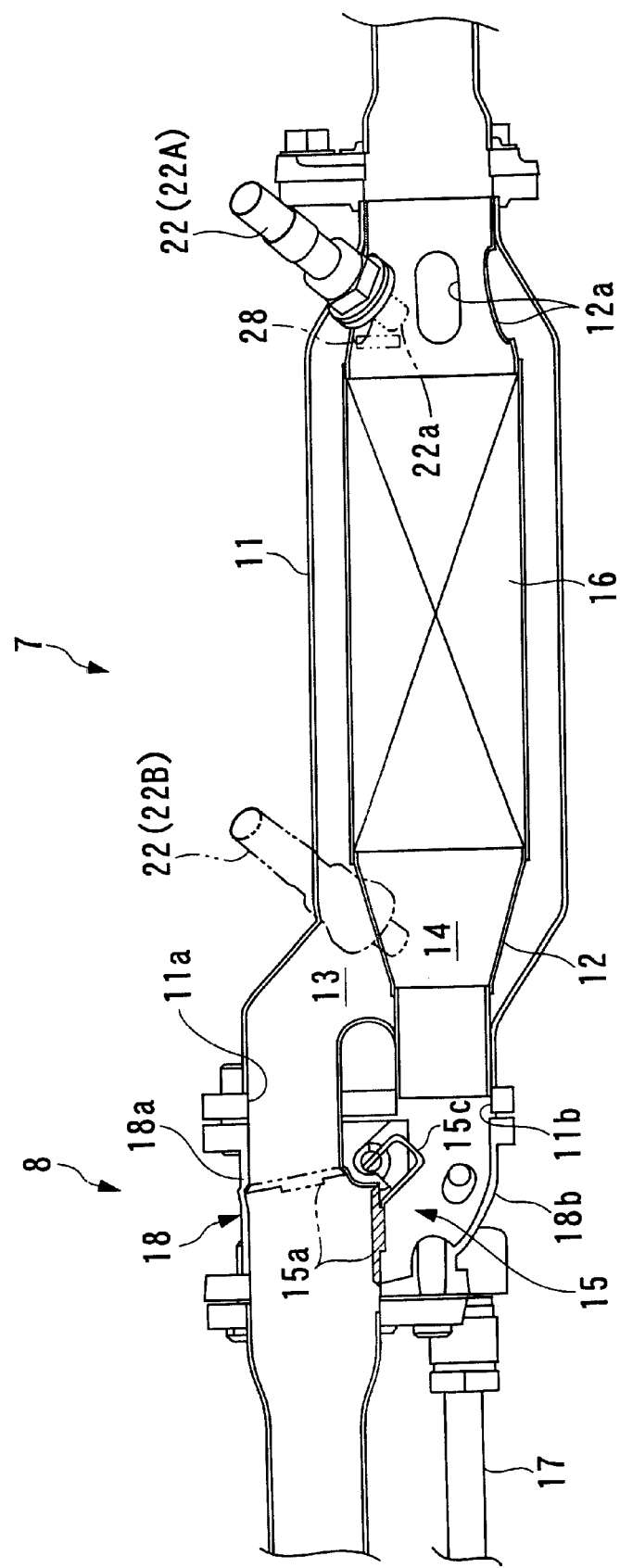
FIG. 2 is an enlarged cross-sectional view showing a hydrocarbon adsorption device.

The hydrocarbon adsorption device 7 is arranged in the exhaust pipe 4 at a location downstream of the catalytic device 6, for adsorbing hydrocarbons in exhaust gases when the engine 1 is in a starting condition (for instance, before approximately 30 to 40 seconds have passed after the start of the engine operation) in which the three-way catalysts 5, 5 remains inactive, to thereby largely reduce emission of hydrocarbons in exhaust gases. Referring to FIGS. 1 and 2, the hydrocarbon adsorption device 7 is connected to the downstream end of the catalytic device 6 via an exhaust passage changeover device 8, and includes a casing 11 forming a generally hollow cylindrical outer shell, a bypass exhaust pipe 12 arranged within the casing 11, and a cylindrical HC adsorber 16 (adsorber) which is filled in an intermediate portion of the bypass exhaust pipe 12 for adsorbing hydrocarbons in exhaust gases flown into the bypass exhaust pipe 12.

As shown in FIG. 2, the casing 11 has an upstream end thereof bifurcated into upper and lower portions. An upper opening 11a of the upper portion of the upstream end communicates with an exhaust passage of the exhaust pipe 4 and with a space (main exhaust passage 13) annular in cross section, formed outside the bypass exhaust pipe 12 in the casing 11, while a lower opening 11b of the lower portion of the upstream end communicates with a space (bypass exhaust passage 14) inside the bypass exhaust pipe 12.

The bypass exhaust pipe 12 has an upstream end thereof inserted into the lower opening 11b of the casing 11 and a downstream end thereof inserted into the downstream end portion of the casing 11, in airtight conditions, respectively. Further, the bypass exhaust pipe 12 is formed with a plurality of (five, for instance) communication slots 12a at locations close to the downstream end at circumferentially equal intervals, via which the downstream end portion of the main exhaust passage 13 and that of the bypass exhaust passage 14, within the casing 11, communicate with each other.

The HC adsorber 16 is formed of a metal honeycomb core, not shown, carrying a zeolite on the surface thereof such that when exhaust gases are passing through the HC adsorber 16, hydrocarbons and water in the exhaust gases are adsorbed by the zeolite. The zeolite which has high heat resistance adsorbs hydrocarbons when it is in a low temperature condition (e.g. lower than 100° C.) while desorbs the hydrocarbons once adsorbed thereby when it is heated to a temperature equal to or higher than a predetermined temperature (e.g. 100 to 250° C.). The desorbed hydrocarbons are recirculated to the engine 1 via an EGR pipe 17 having opposite ends thereof connected to a branch pipe 18b, referred to hereinafter, of the exhaust passage changeover device 8 and an intake pipe 1a of the engine 1, for being burned by the engine 1. Although the zeolite described above is only required to be capable of adsorbing hydrocarbons and water, and is not limited to a particular type, but in the present embodiment, a mixture of USY (Y type), Ga-MFI and ferrierite is employed.

The exhaust passage changeover device 8 is used for connecting the hydrocarbon adsorption device 7 configured as above to the catalytic device 6, and selectively switching the exhaust passage for the exhaust gases having passed through the catalytic device 6 between the main exhaust passage 13 and the bypass exhaust passage 14 depending on a state of activation of the three-way catalysts 5. The exhaust passage changeover device 8 includes a generally hollow cylindrical connection pipe 18 and a changeover valve 15 which is arranged in the connection pipe 18 for switching between the main and bypass exhaust passage. The connection pipe 18 is formed by a main pipe 18a for airtight communication between the downstream end of the catalytic device 6 and the main exhaust passage 13 of the hydrocarbon adsorption device 7, and the branch pipe 18b which is branched from a location upstream of the main pipe 18a, for airtight communication between the downstream end of the catalytic device 6 and the bypass exhaust passage 14 of the hydrocarbon adsorption device 7.

The changeover valve 15 has a disk-shaped valve element 15a and an arm 15c having a predetermined shape and supporting the valve element 15a on one end thereof. As the arm 15c is driven for pivotal movement through a predetermine angle about the other end thereof by a changeover valve driving unit 19 (see FIG. 1) under the control of an ECU 25, referred to hereinafter, the valve element 15a as well is pivotally moved to open one of the main pipe 18a and the branch pipe 18b and close the other of the same. Therefore, as shown in FIG. 2, when the main pipe 18a is opened and at the same time the branch pipe 18b is closed by the valve element 15a, exhaust gases having passed through the catalytic device 6 flow through the main pipe 18a into the main exhaust passage 13 inside the casing 11. Inversely, when the main pipe 18a is closed and at the same time the branch pipe 18b is opened by the valve element 15a (see phantom lines in FIG. 2), exhaust gases having passed through the catalytic device 6 flow through the branch pipe 18b into the bypass exhaust passage 14. It should be noted that the arm 15c has the other end provided with a torsion coiled spring, not shown, by which, as shown in FIG. 2, the valve element 15a normally holds the main pipe 18a in an open state and at the same time the branch pipe 18b in a closed state.

In the exhaust passage changeover device 8 configured as above, normally, the valve element 15a closing the branch pipe 18b is driven for pivotal movement immediately after the start of the engine 1, whereby the branch pipe 18b is opened and at the same time the main pipe 18a is closed. This allows exhaust gases having passed through the catalytic device 6 to be guided into the bypass exhaust passage 14 via the branch pipe 18b, thereby allowing hydrocarbons and water in the exhaust gases to be adsorbed by the HC adsorber 16. The exhaust gases having passed through the HC adsorber 16 further flow downstream so as to be emitted into the atmosphere. As described hereinbelow, when it is determined that the HC adsorber 16 has completed adsorption of hydrocarbons, the valve element 15a which has been closing the main pipe 18a is driven again for pivotal movement to thereby open the main pipe 18a and at the same time close the branch pipe 18b. Thus, exhaust gases having passed through the catalytic device 6 are guided via the main pipe 18a into the main exhaust passage 13 inside the casing 11, flow into the bypass exhaust pipe 12 via the communication slots 12a formed in the downstream end portion of the bypass exhaust pipe 12, and further flow downstream so as to be emitted from the automotive vehicle.

The casing 11 of the hydrocarbon adsorption device 7 has a downstream-side humidity sensor 22A inserted into a downstream and portion thereof, which detects humidity D (hereinafter simply referred to as "the downstream-side humidity D") downstream of the HC adsorber 16 in the bypass exhaust passage 14. The downstream-side humidity sensor 22A supplies an electric signal indicative of the sensed downstream-side humidity D to the ECU 25. The ECU 25 also has an intake air temperature sensor 27 connected thereto for detecting an intake air temperature TA. The ECU 25 (changeover valve drive means, delayed response-compensating means, heater control means, operating condition-detecting means, failure determination execution-judging means, humidity sensor failure-determining means, desorption state-detecting means) controls the engine 1 and the exhaust system 2 including the changeover valve 15 based on the results of detection by the above sensors 22A, 27.

The downstream-side humidity sensor 22A is inserted into the downstream end portion of the casing 11 such that a sensor element 22a mounted on an end of the sensor 22A protrudes into the bypass exhaust passage 14 through one of the communication slots 12a of the bypass exhaust pipe 12, and as described hereinabove, senses the downstream-side humidity D so as to supply the signal indicative of the sensed humidity D to the ECU 25. This signal is dealt with by the ECU 25 as a signal indicative of a relative humidity when conditions for the HC adsorber 16 to adsorb hydrocarbons are satisfied, referred to hereinafter, whereas when the conditions are not satisfied, the signal is dealt with as a signal indicative of an absolute humidity. Further, the downstream-side humidity sensor 22A is provided with a heater 28 for heating the sensor element 22a. The heater 28 is configured such that it is controlled by the ECU 25 so as to be operated for a predetermine time period to heat the sensor element 22a when predetermined conditions, referred to hereinafter, are satisfied. It should be noted that since the downstream-side humidity sensor 22A is described in Japanese Patent Application No. 2000-23085 proposed by the present assignee and hereby incorporated by reference, and hence detailed description thereof is omitted here.

As indicated by phantom lines in FIGS. 1 and 2, in addition to the downstream-side humidity sensor 22A, there may be provided an upstream-side humidity sensor 22B which is the same humidity sensor as the downstream-side humidity sensor 22A, at a location upstream of the HC adsorber 16. This upstream-side humidity sensor 22B detects humidity DF (hereinafter simply referred to as "the upstream-side humidity DF") upstream of the HC adsorber 16 in the bypass exhaust passage 14. It should be noted that in the following description, when the downstream-side humidity sensor 22A and the upstream-side humidity sensor 22B are not distinguished from each other, they are generically referred to as "the humidity sensor 22".

The engine 1 is provided with a crank angle position sensor 32 which delivers a CRK signal and a TDC signal, both of which are respective pulse signals, to the ECU 25 whenever a crankshaft, not shown, of the engine 1 rotates through respective predetermined angles. Each pulse of the TDC signal is generated whenever the crankshaft rotates through 180 degrees, for instance.

The ECU 25 is formed by a microcomputer including an I/O interface, a CPU, a RAM, and a ROM, none of which are specifically shown. Signals from sensors, such as the above humidity sensor 22 and the intake air temperature sensor 27, are each input into the I/O interface for A/D conversion and waveform shaping, and then input into the CPU. The CPU determines an operating condition of the engine 1 based on these signals, according to a control program read from the ROM or the like, and carries out control operations depending on the determined operating condition. It should be noted that when the CPU determines, for instance, that the humidity sensor 22 has failed, the ECU 25 outputs a control signal to a warning lamp 26, whereby the warning lamp 26 is lighted to notify the operator of the failure of the humidity sensor 22.

Figure 3:
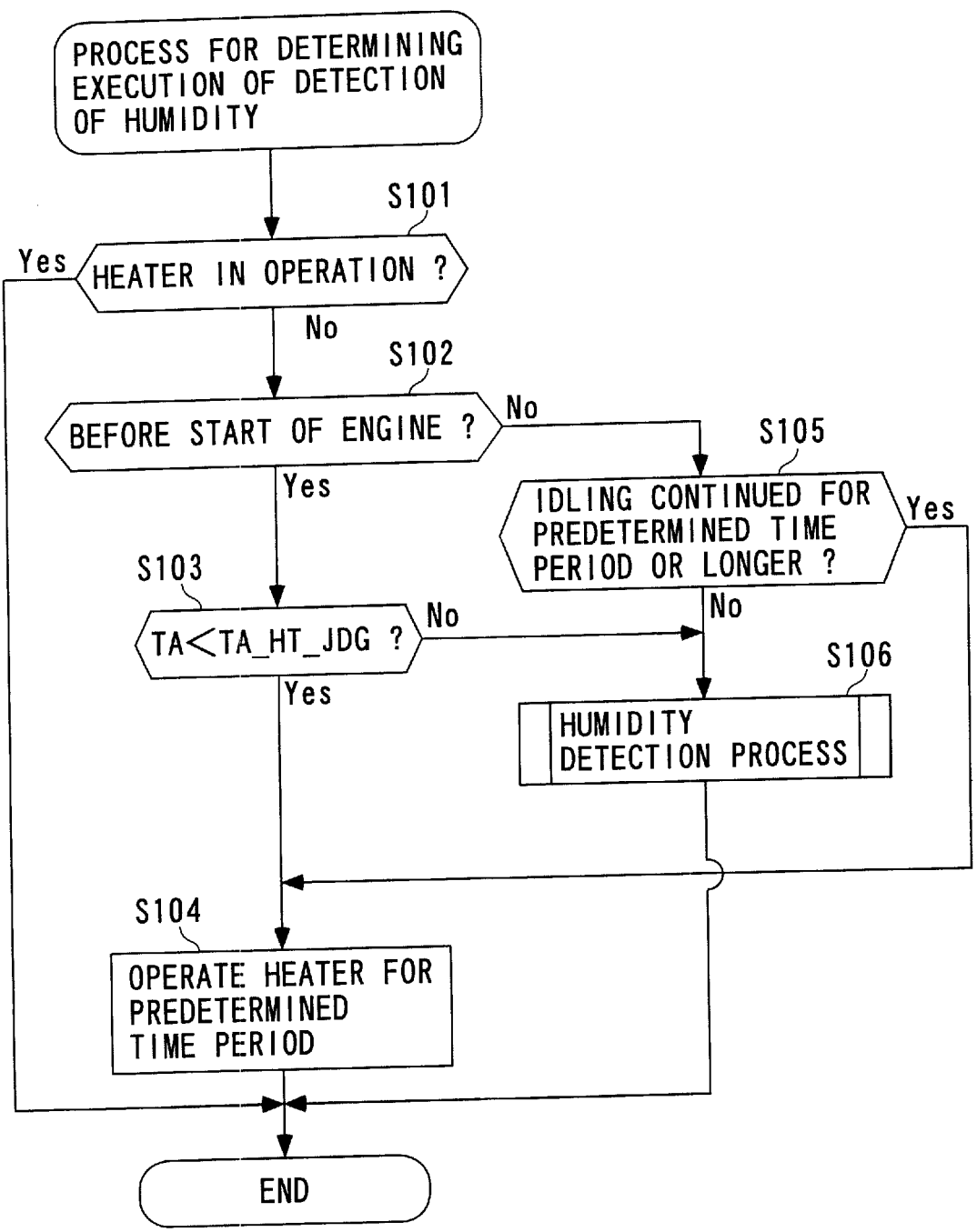
FIG. 3 is a flowchart showing a routine for carrying out a process for determining execution of detection of humidity.

Next, the control operations carried out by the ECU 25 will be described in detail with reference to FIGS. 3 to 13. FIG. 3 shows a process for determining whether or not detection of humidity should be executed. This process is started immediately after an ignition switch, not shown, is turned on to crank the engine 1. In the process, first, it is determined at a step S101 whether or not the heater 28 for heating the humidity sensor 22 is in operation If the answer to this question is affirmative (Yes), i.e. if it is determined that the heater 28 is in operation, the program is immediately terminated, whereas if the answer to the question of the step S101 is negative (No), i.e. if the heater 28 is not in operation, the program proceeds to a step S102, wherein it is determined whether or not it is before the start of the engine 1, more specifically, whether or not cranking of the engine 1 has been started. If the answer to this question is affirmative (Yes), i.e. if it is before the start of the engine 1, the program proceeds to a next step S103, wherein it is determined whether or not the intake air temperature TA sensed by the intake air temperature sensor 27 is lower than a predetermined reference value TA_HT_JDG (50° C., for instance).

If the answer to the question of the step S103 is affirmative (Yes), i.e. if the intake air temperature TA is lower than the reference value TA_HT_JDG, the heater 28 is operated for a predetermined time period (e.g. 10 seconds) at a step S104, followed by terminating the program. The above control of the heater 28 is carried out for the following reason: When an ambient temperature is low at the start of the engine 1, water condensation is liable to occur on the sensor element 22a of the humidity sensor 22, and if detection of humidity is executed in such a state, an actual value of the humidity cannot be sensed with accuracy, so that it is required to eliminate water droplets produced by condensation by operating the heater 28. On the other hand, if the answer to the question of the step S103 is negative (No), i.e. if the intake air temperature TA is equal to or higher than the reference value TA_HT_JDG, it is determined that there is no fear of occurrence of condensation, and a humidity detection process, described in detail hereinafter, is carried out at a step S106, followed by terminating the program.

If the answer to the question of the step S102 is negative (No), i.e. if the engine 1 has already been started, then, the program proceeds to a step S105, wherein it is determined whether or not idling of the engine 1 has continued for a time period equal to or longer than a predetermined time period (e.g. 10 seconds). Condensation can occur on the sensor element 22a of the humidity sensor 22 if idling of the engine 1 has continued for a time period longer than the predetermined time period, and hence if the answer to the question of the step S105 is affirmative (Yes), to remove water droplets from the sensor element 22a similarly to the above, the program proceeds to the step S104, wherein the heater 28 is operated for the predetermined time period (S104), followed by terminating the program. If the answer to the question of the step S105 is negative (No), i.e. if duration of the idling of the engine 1 is shorter than the predetermined time period, the program proceeds to the step S106.

Figure 4:
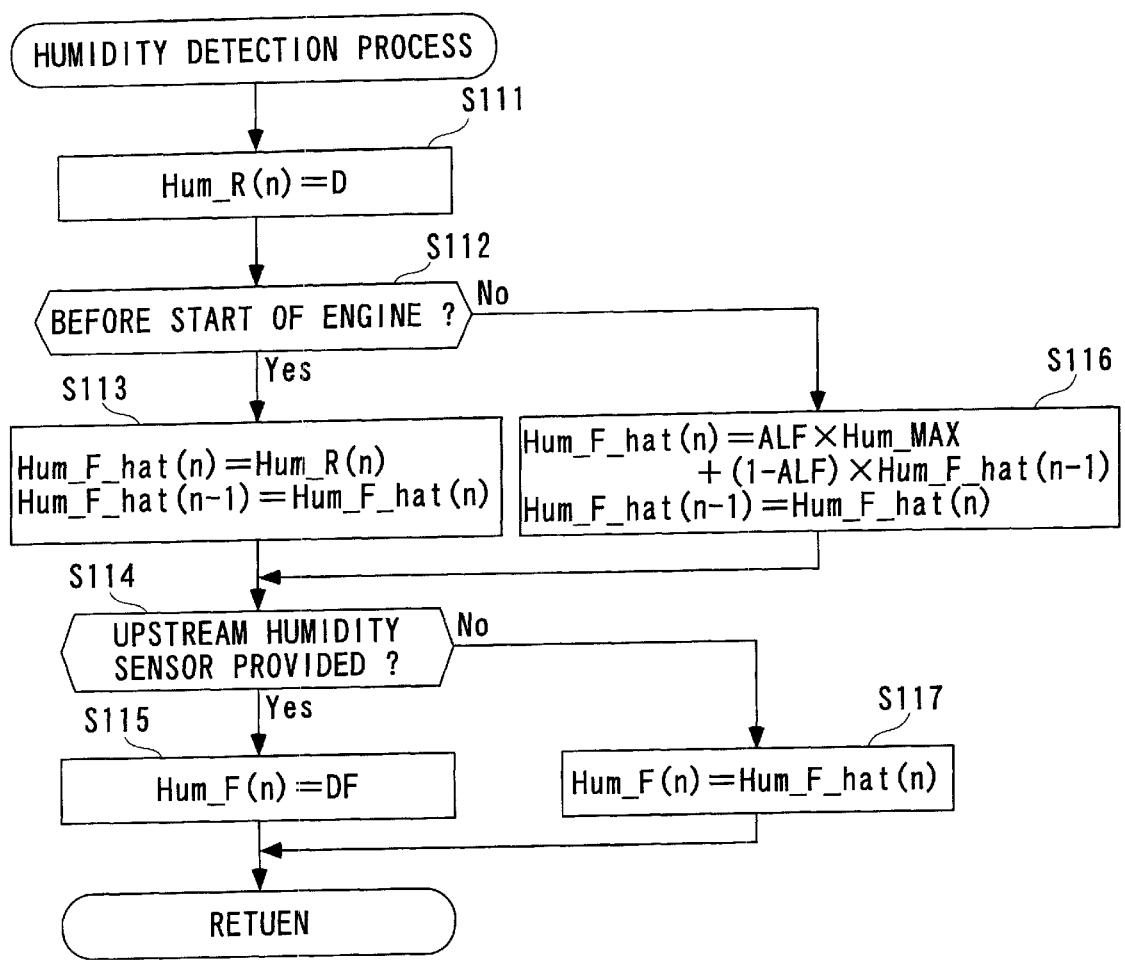
FIG. 4 is a flowchart showing a routine for carrying out a humidity detection process.

FIG. 4 shows the humidity detection process which is carried out at the step S106 based on a result of detection by the humidity sensor 22. In this process, first, at a step S111, a value D detected by the downstream-side humidity sensor 22A is set to the present value Hum_R(n) of the downstream-side humidity.

Next, at a step S112, it is determined whether or not it is before the start of the engine 1. If the answer to this question is affirmative (Yes), i.e. if it is before the start of the engine 1, then, at a step S113, the present value Hum_F_hat(n) of an upstream-side estimated humidity is set to the downstream-side humidity Hum_R(n) set at the step S111. Since exhaust gases from the engine 1 have not yet flown into the bypass exhaust passage 14 before the start of the engine 1, the downstream-side humidity Hum_R(n) is set to the upstream-side estimated humidity Hum_F_hat(n) without further processing. Further, at the step S113, the immediately preceding value Hum_F_hat(n−1) of the upstream-side estimated humidity Hum_F_hat(n) is set to the present value Hum_F_hat(n) thereof.

Thereafter, at a step S114, it is determined whether or not the upstream-side humidity sensor 22B is provided. As indicated by the phantom lines in FIGS. 1 and 2, when the upstream-side humidity sensor 22B is arranged at a location upstream of the HC adsorber 16, the value DF detected by the humidity sensor 22B is set to the present value Hum_F(n) of the upstream-side humidity at a step S115, followed by terminating the program. On the other hand, if the upstream-side humidity sensor 22B is not arranged (NO to S114), the program proceeds to a step S117, wherein the upstream-side estimated humidity Hum_F_hat(n) which has been set at the above step S113 or calculated at a step S116, referred to hereinafter, is set to the upstream-side humidity Hum_F(n), followed by terminating the program.

If the answer to the question of the step S112 is negative (No), i.e. if the engine 1 has already been started, the program proceeds to the step S116, wherein the present value Hum_F_hat(n) of the upstream-side estimated humidity is calculated by using a maximum humidity Hum_MAX which is the maximum value of the relative humidity and the immediately preceding value Hum_F_hat(n−1) of the upstream-side estimated humidity by the following equation (1):

$$Hum\_F\_hat(n) = ALF \times Hum\_MAX + (1-ALF) \times Hum\_F\_hat(n-1) \quad (1)$$

In the above equation (1), ALF designates a weighting coefficient obtained by an experiment, which assumes a value within the range of $0 < ALF < 1.0$. Further, at the step S116, while performing the above-mentioned calculation, the immediately preceding value Hum_F_hat(n−1) of the upstream-side estimated humidity is set to the present upstream-side estimated humidity Hum_F_hat(n) calculated when the present humidity detection process is executed. Then, the program proceeds to the step S114.

As described hereinabove, in the humidity detection process, if the upstream-side humidity sensor 22B is provided, the value DF detected by the humidity sensor 22B is used as the present value Hum_F(n) of the upstream-side humidity, whereas if the upstream-side humidity sensor 22B is not provided, the upstream-side estimated humidity Hum_F_hat(n) estimated at the step S113 or S116 based on the value D detected by the downstream-side humidity sensor 22A is employed.

Figure 5:
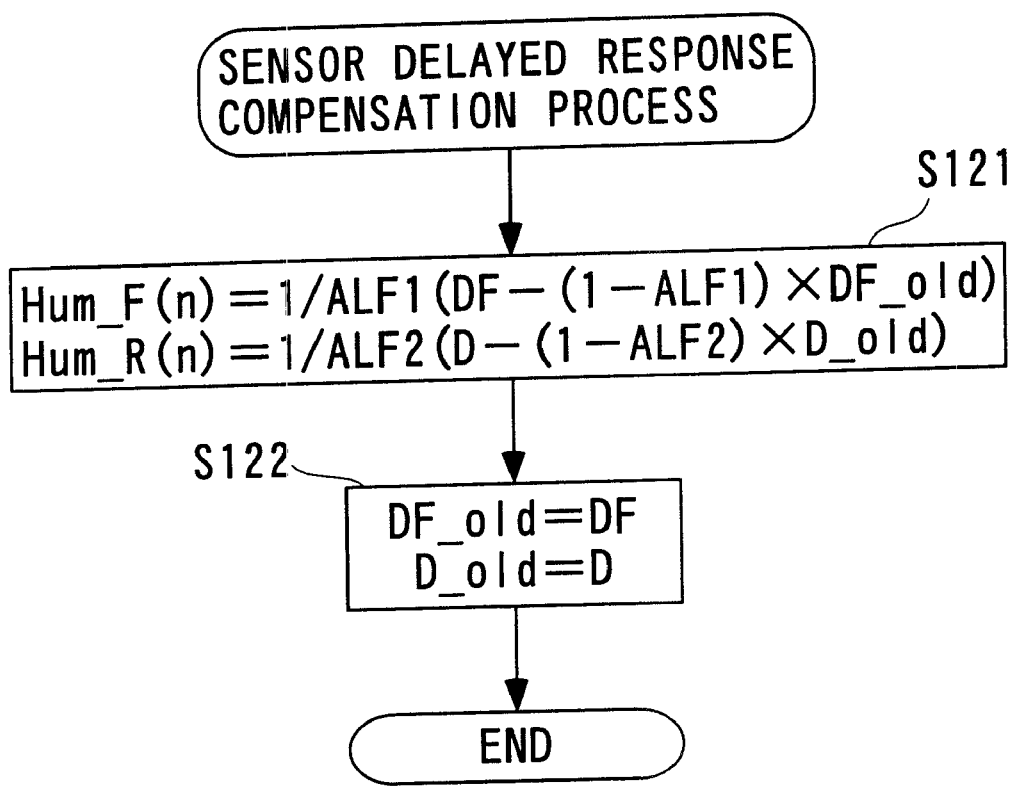
FIG. 5 is a flowchart showing a routine for carrying out a delayed response compensation process for compensating for delayed response of a humidity sensor.

Further, if the humidity sensors 22A, 22B have low responsiveness, a delay in the response of the detected values D, DF occurs, and hence to compensate for the delayed response, a delayed response compensation process shown in FIG. 5 is carried out to compensate for delayed response of the humidity sensor 22. As shown in the figure, in this compensation process, the respective upstream-side humidity Hum_F(n) and downstream-side humidity Hum_R(n) are calculated at a step S121 by using the present detected values D, DF, and immediately preceding detected values D_old, DF_old by the following equations (2) and (3):

$$Hum\_F(n)=1/ALF1(DF-(1-ALF1) \times DF\_old) \quad (2)$$

$$Hum\_R(n)=1/ALF2(D-(1-ALF2) \times D\_old) \quad (3)$$

In the above equations, ALF1 and ALF2 represent correction coefficients for compensating for the delayed response of the humidity sensor 22, which are determined by experiments according to the specification of the humidity sensor 22. The coefficients ALF1 and ALF2 assume values within the ranges of 0<ALF1<1.0 and 0<ALF2<1.0, respectively. The equation (2) can be rewritten, for instance, as follows:

$$Hum\_F(n)=1/ALF1(DF-DF\_old)+DF\_old$$

As clearly shown by this equation, as the correction coefficients ALF1, ALF2 become larger, the degree of compensation is reduced, and as the values of the ALF1 and ALF2 draw closer to 1, the upstream-side humidity Hum_F(n) and the downstream-side humidity Hum_R(n) draw infinitely closer to the present values DF, D. On the other hand, as the correction coefficients ALF1, ALF2 become smaller, the degree of compensation is increased.

Then, at a step S122, the present values DF and D are set to the immediately preceding values DF_old and D_old, respectively, so as to be used as the immediately preceding values when the next compensation process is executed, followed by terminating the program. It should be noted that if both of the humidity sensors 22A, 22B are highly responsive, the values D, DF detected thereby are used as the downstream-side humidity Hum_R(n) and the upstream-side humidity Hum_F(n), respectively, without further processing, and the above-mentioned compensation process is not carried out.

Figure 6A:
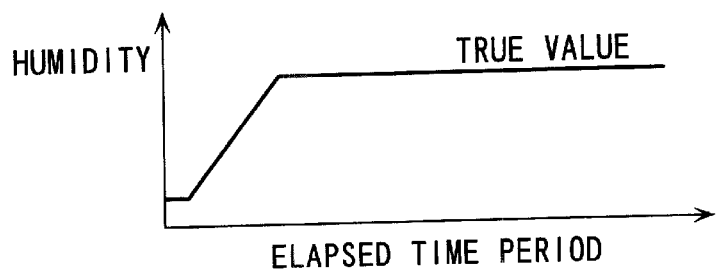
Figure 6B:
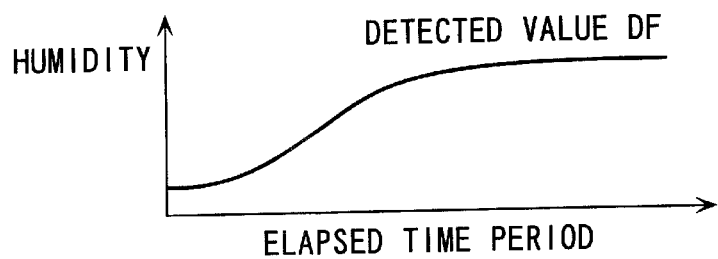
Figure 6C:
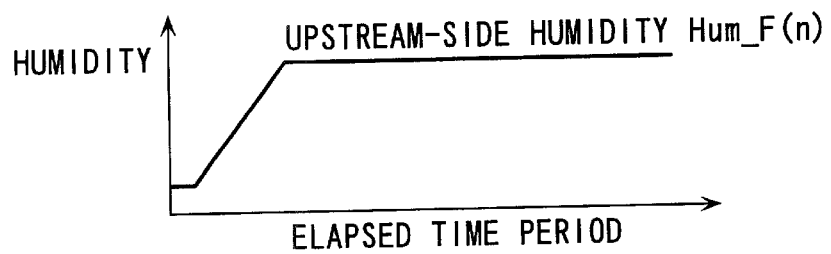

FIGS. 6A, 6B and 6C show examples of changes in (true value) of the humidity on the upstream side of the HC adsorber 16, the value DF detected by the upstream-side humidity sensor 22B, and the upstream-side humidity Hum_F(n) obtained by correcting the detected value DF for the compensation, respectively. As shown in FIG. 6A, for instance, assuming that after the start of the engine 1, the humidity of exhaust gases from the engine 1 is varied such that it rises immediately after the start of the engine, and then becomes substantially fixed, if the humidity of the exhaust gases is detected by a humidity sensor having low responsiveness, as shown in FIG. 6B, the detected value DF is changed in a manner delayed from the change of the true value. On the other hand, in the case of the upstream-side humidity Hum_F(n) which is calculated by the above equation (2), a humidity value can be obtained which is changed with approximately the same timing as that of the true value, whereby it is possible to compensate for the delayed response of the upstream-side humidity sensor 22B.

It should be noted that if the upstream-side humidity sensor 22B is not provided, for instance, the downstream-side humidity Hum_R(n) calculated at the step S121 in FIG. 5 for compensation is used at the steps S113, S116 in FIG. 4, thereby making it possible to obtain a corrected and proper upstream-side humidity Hum_F(n).

Figure 7:
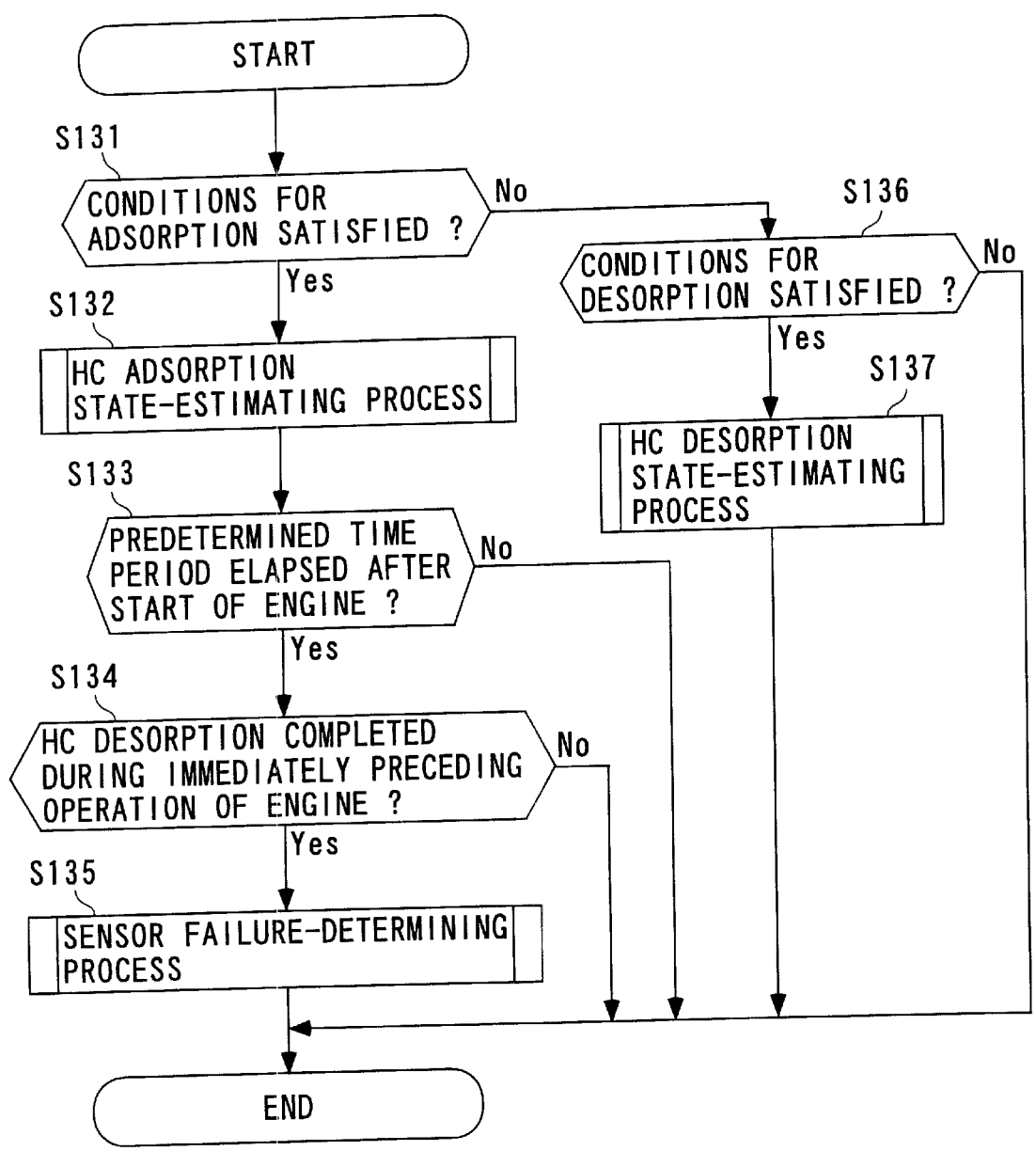
FIG. 7 is a flowchart showing a main routine for carrying out estimation processes for estimating a state of adsorption of hydrocarbons by the HC adsorber and a state of desorption of hydrocarbons from the HC adsorber, and a failure determination process for determining failure of the humidity sensor.

FIG. 7 shows a main routine for carrying out estimation processes for estimating a state of adsorption of hydrocarbons by the HC adsorber 16 and a state of desorption of hydrocarbons from the HC adsorber 16, and a failure determination process for determining failure of the humidity sensor 22. The estimation process for estimating the state of adsorption of hydrocarbons by the HC adsorber 16 is executed in synchronism with input of the TDC signal from the crank angle position sensor 32 to the ECU 25. In this estimation process, first, it is determined at a step S131 whether or not the conditions for the HC adsorber 16 to adsorb hydrocarbons are satisfied. More specifically, it is determined whether or not the valve element 15a of the changeover valve 15 is held in a state closing the main exhaust passage 13 and at the same time opening the bypass exhaust passage 14, as indicated by the phantom lines in FIG. 2, that is, in a state guiding exhaust gases from the engine 1 into the bypass exhaust passage 14.

Figure 8:
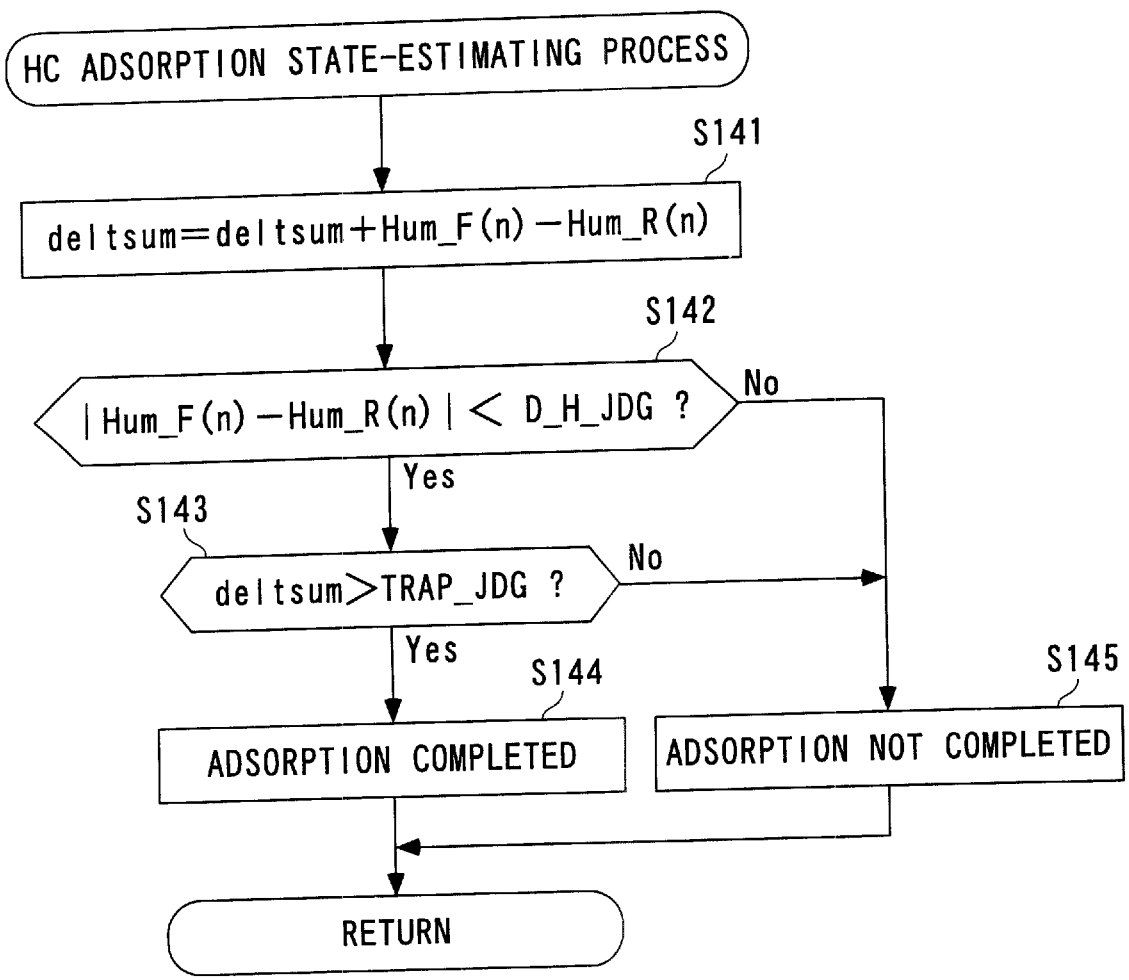
FIG. 8 is a flowchart showing a subroutine for carrying out the estimation process for estimating the state of adsorption of hydrocarbons by the HC adsorber.

If the answer to the question of the step S131 is affirmative (Yes), i.e. if the above adsorbing conditions are satisfied, the program proceeds to a step S132 wherein the estimation process is executed to estimate the state of adsorption of hydrocarbons. FIG. 8 is a flowchart showing a subroutine for carrying out the estimation process for estimating the state of adsorption of hydrocarbons by the HC adsorber 16. In this process, first, by using the upstream-side humidity Hum_F(n) and the downstream-side humidity Hum_R(n) calculated in the FIG. 4 humidity detection process, the cumulative value deltsum of differences between the upstream-side and downstream-side humidity values is calculated at a step S141 by the following equation (4):

$$deltsum=deltsum+Hum\_F(n)-Hum\_R(n) \quad (4)$$

Figure 9:
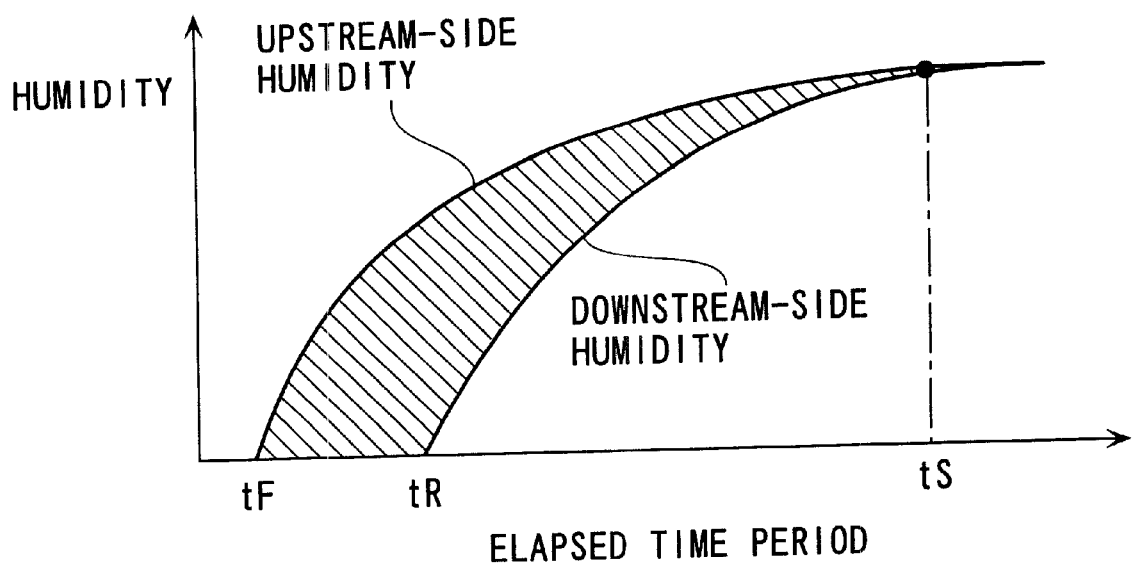
FIG. 9 is a timing chart showing an example of changes in the upstream-side humidity and downstream-side humidity from a time of the start of the engine.

When the engine 1 is started, the upstream-side humidity and the downstream-side humidity are normally changed as shown in FIG. 9. More specifically, the upstream-side humidity rises prior to the downstream-side humidity (time tF), and is changed such that the value thereof is increased as time elapses, and eventually converged to a fixed value. On the other hand, the downstream-side humidity rises later than the upstream-side humidity after the upstream-side humidity has risen to a certain level (time tR). Then, the value of the downstream-side humidity is increased as time elapses, and when the HC adsorber 16 has completed the adsorption of hydrocarbons (time tS), it is converged to approximately the same value as that of the upstream-side humidity. Therefore, by repeatedly executing the present estimation process, the cumulative value deltsum, that is, the area of a hatched portion shown in FIG. 9 is calculated by the above equation (4), which corresponds to the amount of water adsorbed by the HC adsorber 16. The amount of the adsorbed water is proportional to the amount of hydrocarbons adsorbed by the HC adsorber 16, and has close correlation with the same.

Then, the program proceeds to a step S142, wherein it is determined whether or not the absolute value of the difference between the upstream-side humidity Hum_F(n) and the downstream-side humidity Hum_R(n) is smaller than a predetermined reference value D_H_JDG (e.g. 10%). If the answer to this question is negative (No), it is determined at a step S145 that the HC adsorber 16 has not yet completed the adsorption of hydrocarbons since the difference between the upstream-side humidity Hum_F(n) and the downstream-side humidity Hum_R(n) is large, and the present program is terminated. On the other hand, if the answer to the question of the step S142 is affirmative (Yes), i.e. if it is determined that the difference between the upstream-side humidity Hum_F(n) and the downstream-side humidity Hum_R(n) is small, the program proceeds to a step S143.

At the step S143, it is determined whether or not the cumulative value deltsum calculated at the step S141 is larger than a predetermined reference value TRAP_JDG (e.g. 2000%). If the answer to this question is negative (No), it is determined at the step S145 that the HC adsorber 16 has not yet completed the adsorption of hydrocarbons since the cumulative value deltsum is small, followed by terminating the program, whereas if the answer to the question of the step S143 is affirmative (Yes), i.e. if the cumulative value deltsum is larger than the reference value TRAP_JDG, it is determined at a step S144 that the HC adsorber 16 has completed the adsorption of hydrocarbons, followed by terminating the program.

As described hereinabove, in the present estimation process, if the difference between the upstream-side humidity Hum_F(n) and the downstream-side humidity Hum_R(n) is smaller than the reference value D_H_JDG, and at the same time the cumulative value deltsum is larger than the reference value TRAP_JDG, it is determined that the HC adsorber 16 has completed the adsorption of hydrocarbons. As described above, during the start of the engine 1, the above difference is progressively decreased as the adsorption of hydrocarbons by the HC adsorber 16 is nearing completion, and the cumulative value deltsum has close correlation with the amount of hydrocarbons adsorbed by the HC adsorber 16. Therefore, by carrying out the above process, the state of adsorption of hydrocarbons by the HC adsorber 16, that is, whether or not the adsorption of hydrocarbons by the HC adsorber 16 has been completed can be properly determined based on the result(s) of detection by the downstream-side humidity sensor 22A or the sensor 22A and the upstream-side humidity sensor 22B.

Following the estimation process for estimating the state of adsorption of hydrocarbons at the step 132, the program proceeds to a step S133 in FIG. 7, wherein it is determined whether or not a predetermined time period (e.g. 10 seconds) has elapsed after the start of the engine 1. Then, at a step S134, it is determined whether or not desorption of hydrocarbons from the HC adsorber 16, described hereinafter, had been completed during the immediately preceding operation of the engine 1 (at a time point of termination of the operation). If either of the answers to these questions is negative (No), it is determined that conditions for executing the failure determination process for determining failure of the humidity sensor 22 are not satisfied, followed by terminating the program. On the other hand, if both of the answers to the questions of the steps S133 and S134 are affirmative (Yes), it is determined that the conditions for executing the failure determination process are satisfied, and this process is carried out at a step S135.

As described hereinabove, to execute the failure determination process for determining failure of the humidity sensor 22, the determinations at the steps S133 and S134 are carried out for the following reasons: First, at the step S133, the lapse of a predetermined time period after the start of the engine 1 is set to a requirement for performing the failure determination process at the step s133, because only after a certain time period has elapsed after the start of the engine 1, the adsorption of hydrocarbons by the HC adsorber 16 nears completion, whereby the humidity value detected by the humidity sensor 22 (see FIGS. 9 and 11B) becomes stable at a substantially fixed value. Therefore, by executing determination of failure of the humidity sensor 22 when the detected value is stable or substantially fixed, it is possible to carry out an appropriate determination of the failure of the humidity sensor 22. On the other hand, completion of desorption of hydrocarbons during the preceding operation of the engine 1 is set to a requirement at the step S134, because if desorption of hydrocarbons had not been completed during the preceding operation of the engine 1, manners of changes in value detected by the humidity sensor 22 become different to advance or retard timing of proper execution of the failure determination. In such a case, the failure determination is not executed, but only when desorption of hydrocarbons had been completed during the immediately preceding operation of the engine 1, the failure determination is carried out, whereby it is possible to prevent erroneous failure determination of the humidity sensor 22.

Figure 10:
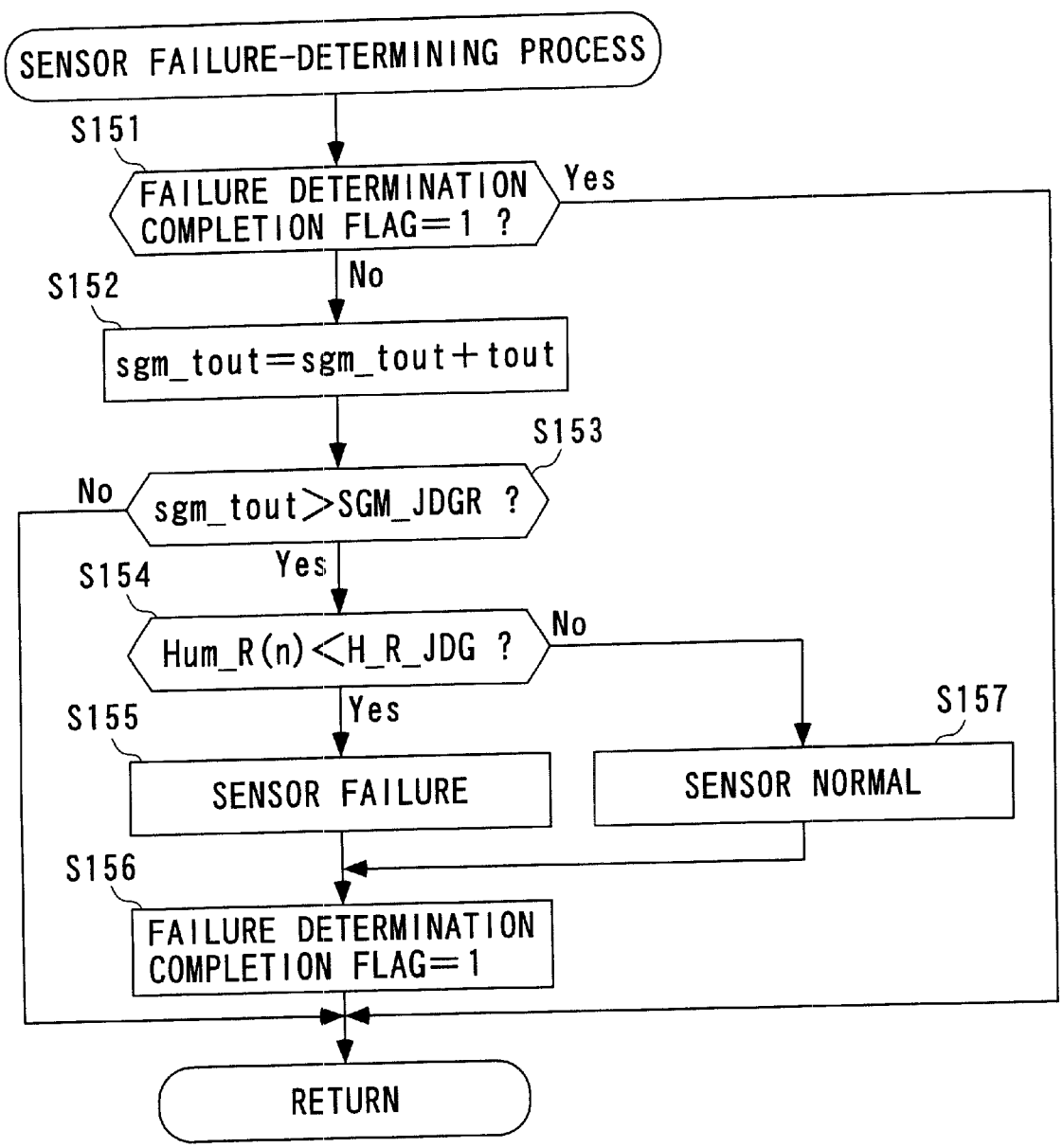
FIG. 10 is a flowchart showing a subroutine for carrying out the failure determination process for determining failure of the humidity sensor.

FIG. 10 is a flowchart showing a subroutine for carrying out the failure determination process carried out at the step S135, for determining whether or not the failure of the downstream-side humidity sensor 22A has occurred. In this process, first, it is determined at a step S151 whether or not a failure determination completion flag assumes 1. The failure determination completion flag is reset to 0 when the ignition switch is turned on, and set to 1 at a step S156, referred to hereinafter, when the failure determination of the downstream-side humidity sensor 22A has been completed. If the answer to the question of the step S151 is affirmative (Yes), i.e. if the failure determination completion flag assumes 1, the program is immediately terminated. As described above, if the failure determination of the downstream-side humidity sensor 22A has already been completed, the failure determination process is not carried out thereafter. That is, this failure determination is carried out only once when the engine 1 is started.

If the answer to the question of the step S151 is negative (No), i.e. if in the present process, the failure determination of the downstream-side humidity sensor 22A has not been completed, a cumulative value sgm_tout of the fuel injection time period tout of all the cylinders of the engine 1 is calculated by the following equation:

$$sgm\_tout = sgm\_tout + tout \quad (5)$$

The above equation is employed to estimate the total amount of heat provided to the exhaust system 2 from the engine from the time of the start thereof.

Then, it is determined at a step S153 whether or not the cumulative value sgm_tout is larger than a predetermined reference value SGM_JDGR. If the answer to this question is negative (No), it is determined that the total amount of heat is not large enough to sufficiently elevate the temperature of the sensor element 22a of the downstream-side humidity sensor 22A, and the program is immediately terminated without carrying out the failure determination of the downstream-side humidity sensor 22A.

Figure 11A:
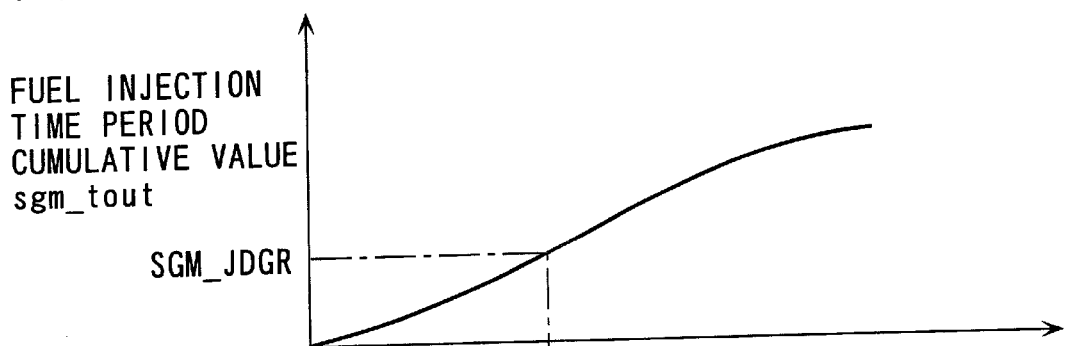

On the other hand, if the answer to the question of the step S153 is affirmative (Yes), it is determined that the temperature of the sensor element 22a has been sufficiently elevated, and the program proceeds to a step S154, wherein it is determined whether or not the downstream-side humidity Hum_R(n) is smaller than the reference value D_H_JDG (e.g. 90%). As shown in FIG. 11A, the cumulative value sgm_tout is increased as time elapses from the time of the start of the engine 1, and when the same exceeds the reference value SGM_JDGR (time tK), the temperature of the sensor element 22ahas been sufficiently elevated, and the adsorption of hydrocarbons by the HC adsorber 16 has been completed or is nearing completion, so that the downstream-side humidity Hum_R(n) assumes a substantially fixed value. The above reference value H_R_JDGR is set to a predetermined value slightly smaller than such a fixed value. Therefore, if the answer to the question of the step S154 is negative (No), i.e. if the value of the downstream-side humidity Hum_R(n) is equal to or larger than the reference value H_R_JDGR, it is determined that the downstream-side humidity sensor 22A is normal, whereas if the answer to the question of the step S154 is affirmative (Yes), i.e. if the value of the downstream-side humidity Hum_R(n) is smaller than the reference value H_R_JDGR, it is determined that the downstream-side humidity sensor 22A has failed. Then, the failure determination completion flag is set to 1 at a step S156, followed by terminating the program.

By carrying out the above process, it is possible to properly carry out the failure determination of the downstream-side humidity sensor 22A based on the result of detection by the downstream-side humidity sensor 22A itself. It should be noted that if the upstream-side humidity sensor 22B is provided, a failure determination process therefor can be carried out similarly to the failure determination of the downstream-side humidity sensor 22A simply by changing the aforementioned two reference values (SGM_JDGR, H_R_JDG) in magnitude.

Figure 12:
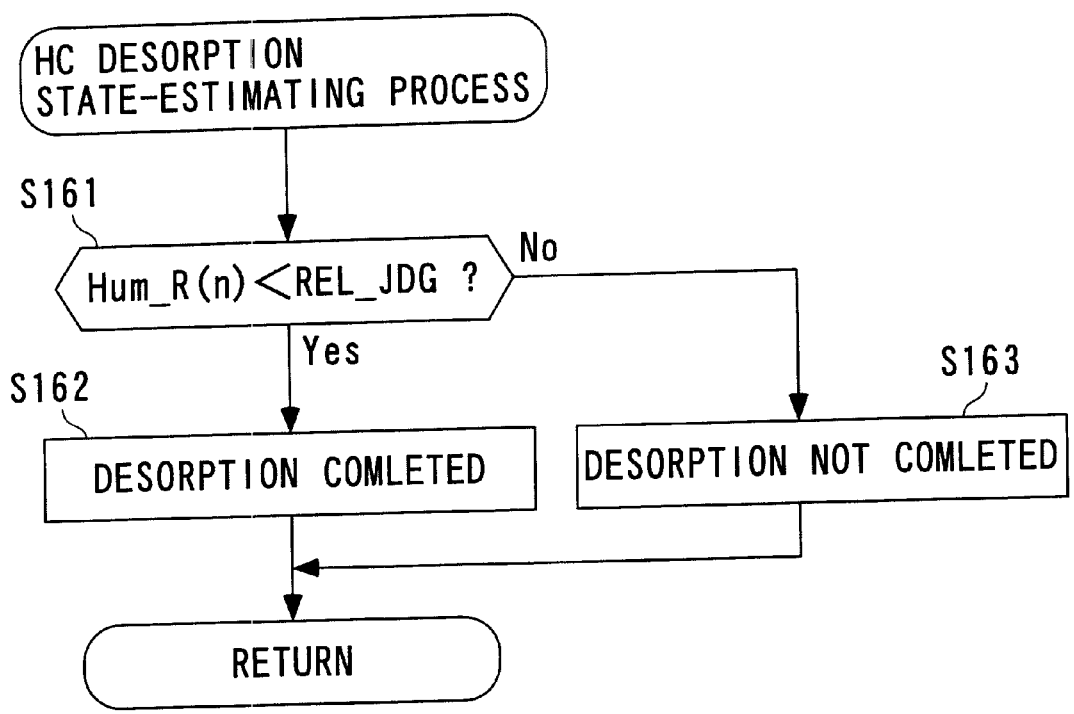
FIG. 12 is a flowchart showing a subroutine for carrying out an estimation process for estimating a state of desorption of hydrocarbons from the HC adsorber.

Referring again to FIG. 7, if the answer to the question of the step S131 is negative (No), i.e. if the conditions of the adsorption are not satisfied, the program proceeds to a step S136, wherein it is determined whether or not conditions for the HC adsorber 16 to desorb hydrocarbons are satisfied. More specifically, it is determined whether or not an EGR operation is being executed. If the answer to the question of the step S136 is affirmative (Yes), i.e. if the conditions for the HC adsorber 16 to desorb hydrocarbons are satisfied, the program proceeds to a step S137, wherein the estimation process for estimating the state of desorption of hydrocarbons from the HC adsorber 16 is executed. FIG. 12 shows a subroutine for carrying out the above estimation process for estimating the state of desorption of hydrocarbons from the HC adsorber 16. In the present process, it is determined at a step S161 whether or not the downstream-side humidity Hum_R(n) is smaller than a predetermined reference value REL_JDG (e.g. 15%).

Figure 11B:
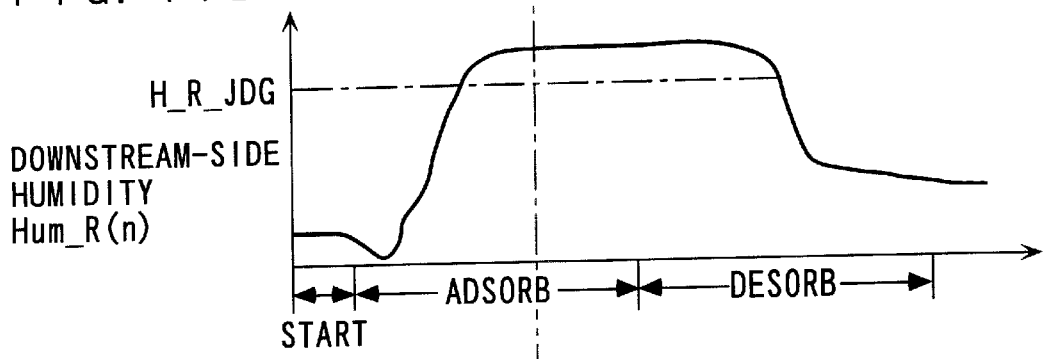
Figure 11C:
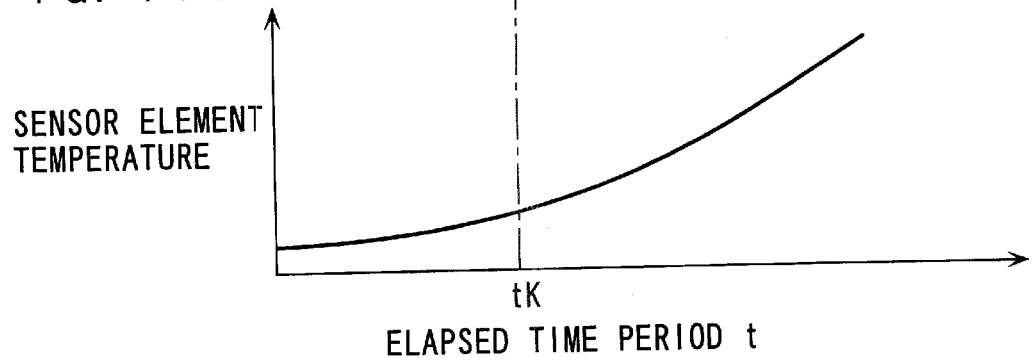

Referring to FIG. 11B, when hydrocarbons start to be desorbed from the HC adsorber 16, at the beginning, water is desorbed from the HC adsorber 16 together with hydrocarbons, whereby the downstream-side humidity Hum_R(n) holds an approximately fixed value, and then as the amount of water remaining in the HC adsorber 16 is decreased, the amount of desorption thereof is reduced, which leads to reduction of the downstream-side humidity Hum_R(n). As a result, if the answer to the question of the step S161 is affirmative (Yes), i.e. if the downstream-side humidity Hum_R(n) is smaller than the reference value REL_JDG, it is determined at a step S162 that the downstream-side humidity Hum_R(n) is small, and the desorption of hydrocarbons from the HC adsorber 16 has been completed, followed by terminating the program. On the other hand, if the answer to the question of the step S161 is negative (No), i.e. if the downstream-side humidity Hum_R(n) is equal to or larger than the reference value REL_JDG, it is determined at a step S163 that the desorption of the hydrocarbons has not yet been completed, followed by terminating the program.

By carrying out the estimation process described hereinabove, it is possible to appropriately determine that the desorption of hydrocarbons from the HC adsorber 16 has been completed, based on the result of detection by the downstream-side humidity sensor 22A.

Figure 13:
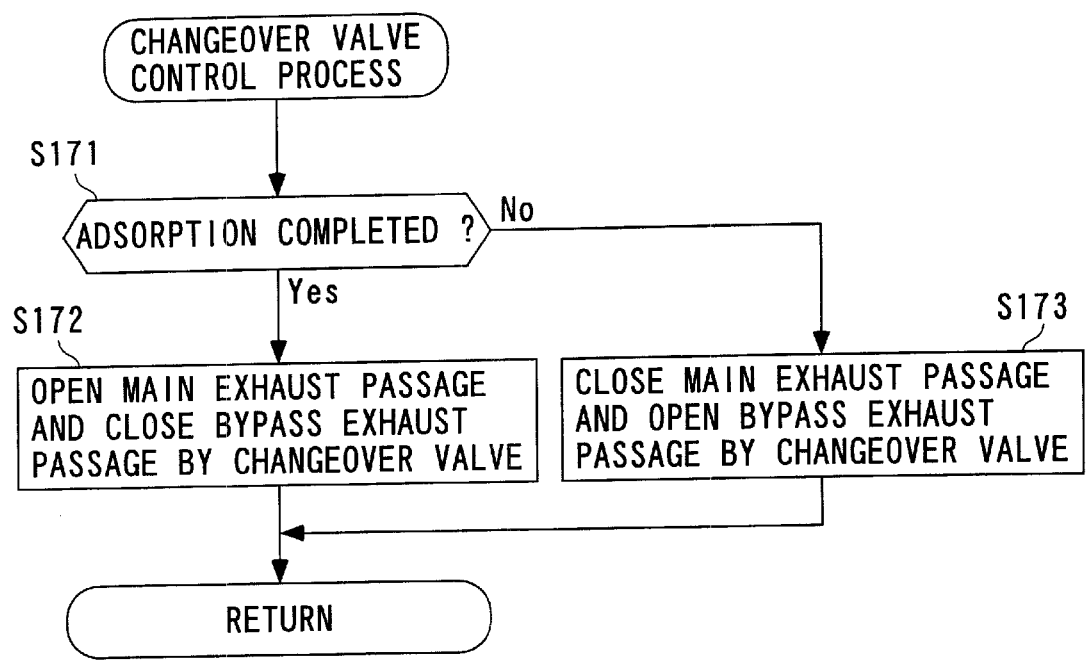
FIG. 13 is a flowchart showing a routine for carrying out a control process for controlling a changeover valve.

FIG. 13 shows a routine for carrying out a control process for controlling the changeover valve, by which the exhaust passage is selectively switched between the main exhaust passage 13 and the bypass exhaust passage 14. In this process, it is determined at a step S171 whether or not the adsorption of hydrocarbons by the HC adsorber 16 has been completed. This determination is made based on whether or not the step S144 described hereinabove with reference to FIG. 8 is carried out. If the answer to the question of the step S171 is negative (No), it means that the adsorption of hydrocarbons by the HC adsorber 16 has not yet been completed, i.e. that the HC adsorber 16 is in the course of adsorbing hydrocarbons, and hence the changeover valve 15 is held as it is. More specifically, at a step S173, the valve element 15a of the changeover valve 15 is held in a state closing the main exhaust passage 13 and at the same time opening the bypass exhaust passage 14.

If the answer to the question of the step S171 is affirmative (Yes), it means that the adsorption of hydrocarbons by the HC adsorber 16 has been completed. Hence, the main exhaust passage 13 is opened and at the same time the bypass exhaust passage 14 is closed by the valve element 15a of the changeover valve 15 at a step S172. It should be noted that the EGR operation is executed by using the EGR pipe 17 thereafter to thereby desorb hydrocarbons from the HC adsorber 16.

By carrying out the above control process, the changeover valve 15 can be switched with appropriate timing based on the result of detection by the downstream-side humidity sensor 22A.

As described above in detail, according to the present embodiment, it is possible to properly estimate the state of adsorption of hydrocarbons by the HC adsorber 16, that is, whether or not adsorption of hydrocarbons by the HC adsorber 16 has been actually completed, based on the downstream-side humidity Hum_R(n) which has close correlation with an actual state of adsorption of hydrocarbons by the HC adsorber 16. Further, it is possible to control the changeover valve 15 with appropriate timing by switching the same according to the state of adsorption of hydrocarbons by the HC adsorber 16, which enables exhaust gases to be sufficiently purified.

Further, the delayed response of the humidity sensor 22 can be compensated for, whereby even if the humidity sensor 22 has low responsiveness, it is possible to switch the changeover valve 15 with more suitable timing by compensating for the delayed response of the humidity sensor 22. Furthermore, by heating the sensor element 22a of the humidity sensor 22 using the heater 28 depending on the operating condition of the engine 1, it is possible to place the sensor element 22a in a state suitable for detecting humidity. As a result, it is possible to avoid occurrence of inconveniences, such as condensation formed on the sensor element 22a and deposition of coke or soot thereon, thereby properly detecting the humidity.

Furthermore, according to the failure determination device for the humidity sensor of the present invention, it is possible to properly estimate the state of adsorption of hydrocarbons by the HC adsorber 16 and the state of desorption of hydrocarbons from the HC adsorber 16, based on the downstream-side humidity Hum_R(n) which has close correlation with an actual state of adsorption of hydrocarbons by the HC adsorber 16. Further, the failure determination of the humidity sensor 22 can be properly executed based on the result of detection by the same with appropriate timing based on the estimated state of adsorption of hydrocarbons by the HC adsorber 16 and the state of desorption of hydrocarbons from the HC adsorber 16. Moreover, the failure determination of the humidity sensor 22 is executed by using a humidity value detected by the sensor 22, and hence it is possible to implement the failure determination device for determining failure of the humidity sensor by relatively simple construction without any need for a special device.

It should be noted that the invention is not limited to the embodiment described above, but it can be practiced in various ways. For instance, although in the above embodiment, the catalytic device 6 containing the three-way catalysts 5, and the hydrocarbon adsorption device 7 containing the HC adsorber 16 are arranged separately from each other in the exhaust pipe 4 as exhaust gas purification catalysts, this is not limitative but the present invention can be applied to an exhaust gas purification catalyst of a so-called hybrid type in which these devices are configured as a single or unitary device. Further, the humidity sensor 22 can be integrated with an air-fuel ratio sensor by accommodating them in the same housing.

It is further understood by those skilled in the art that the foregoing is a preferred embodiment of the invention, and that various changes and modifications may be made without departing from the spirit and scope thereof.

What is claimed is:

1. A failure determination device for a humidity sensor that detects humidity of exhaust gases from an internal combustion engine, the failure determination device comprising:
operating condition-detecting means for detecting an operating condition of the engine;
failure determination execution-judging means for judging whether or not the engine is in a predetermined operating condition in which failure determination of the humidity sensor can be executed, based on a result of detection by said operating condition-detecting means; and
humidity sensor failure-determining means for determining whether or not the humidity sensor has failed, based on a result of detection by the humidity sensor, when said failure determination execution-judging means judged that the failure determination of the humidity sensor can be executed engine is in said predetermined operating condition.

2. A failure determination device according to claim 1, wherein an exhaust passage for the exhaust gases is configured such that to switch the exhaust passage can be switched between a main exhaust passage and a bypass exhaust passage having an adsorber arranged in an intermediate portion thereof, the adsorber being capable of for adsorbing hydrocarbons and water in the exhaust gases, the humidity sensor being arranged at a location downstream of the adsorber in the bypass exhaust passage, and
wherein said failure determination execution-judging means judges that the failure determination of the humidity sensor can be executed engine is in said predetermined operating condition when the exhaust passage has been switched to the bypass exhaust passage, and at the same time the adsorber is adsorbing hydrocarbons in the exhaust gases guided into the bypass exhaust passage.

3. A failure determination device according to claim 2, wherein the hydrocarbons are desorbed from the adsorber by switching the exhaust passage to the main exhaust passage, the failure determination device further comprising desorption state-detecting means for detecting a state of desorption of the hydrocarbons from the adsorber,
wherein said failure determination execution-judging means judges whether or not the failure determination of the humidity sensor can be executed engine is in said predetermined operation condition, based on the state of the desorption of the hydrocarbons from the adsorber at a time of termination of a preceding operation of the engine, detected by the desorption state-detecting means.

4. A failure determination device according to claim 2, wherein said failure determination execution-judging means further includes timer means for measuring a time period after a start of the engine, and determines whether or not failure determination of the humidity sensor can be executed the engine is in said predetermined operating condition further based on the time period measured by said timer means.

5. A failure determination device according to claim 3, wherein said failure determination execution-judging means further includes fuel injection time-integrating means for calculating a cumulative value of fuel injection time periods after a start of the engine, and determines whether or not failure determination of the humidity sensor can be executed the engine is in said predetermined operating condition further based on the cumulative value calculated by said fuel injection time-integrating means.

6. A failure determination device according to claim 1, wherein said humidity sensor failure-determining means determines that the humidity sensor has failed when the value of humidity detected by the humidity sensor is lower than a predetermined value.

7. A control system for controlling an exhaust passage changeover valve of an internal combustion engine, the changeover valve switching an exhaust passage having a catalytic device arranged therein for purifying exhaust gases from the engine between a main exhaust passage and a bypass exhaust passage bypassing the main exhaust passage and having an adsorber arranged therein which is capable of adsorbing hydrocarbons and water in the exhaust gases, the control system comprising:
a humidity sensor arranged at a location downstream of the adsorber in the bypass exhaust passage, for detecting humidity of the exhaust gases guided into the bypass exhaust passage; and
changeover valve drive means for driving the changeover valve based on a result of detection by said humidity sensor.

8. A control system according to claim 7, further comprising delayed response compensation means for compensating for a delayed response of said humidity sensor.

9. A control system according to claim 7, wherein said humidity sensor includes a sensor element for being exposed to the exhaust gases for detecting humidity thereof, the control system further comprising:
a heater for heating said sensor element;
operating condition-detecting means for detecting an operating condition of the engine; and
heater control means for controlling an operation of said heater depending on the operating condition detected by said operating condition-detecting means.

10. A control system according to claim 7, further comprising upstream-side humidity-estimating means for estimating humidity at a location upstream of the adsorber, based on a value of the humidity detected by said humidity sensor.

11. A control system according to claim 10, wherein said changeover valve drive means drives the changeover valve based on a difference between the value of the humidity detected by said humidity sensor and a value of the humidity estimated by said upstream-side humidity-estimating means.

12. A control system according to claim 11, wherein said changeover valve drive means drives the changeover valve further based on a cumulative value of the difference between the value of the humidity detected by said humidity sensor and the value of the humidity estimated by said upstream-side humidity-estimating means.

13. A control system according to claim 7, further comprising an upstream-side humidity sensor for detecting humidity at a location upstream of the adsorber.

14. A control system according to claim 10, wherein said changeover valve drive means drives the changeover valve based on a difference between a value of the humidity detected by said humidity sensor and a value of the humidity detected by said upstream-side humidity sensor.

15. A control system according to claim 11, wherein said changeover valve drive means drives the changeover valve further based on a cumulative value of the difference between the value of the humidity detected by said humidity sensor and the value of the humidity detected by said upstream-side humidity sensor.

* * * * *